(12) United States Patent
Jensen et al.

(10) Patent No.: US 7,745,066 B2
(45) Date of Patent: Jun. 29, 2010

(54) METHOD FOR PREPARING SOLID MATERIALS COMPRISING IMMOBILIZED PROTEORHODOPSIN

(75) Inventors: Rasmus B. Jensen, Mountain View, CA (US); Bradley R. Kelemen, Menlo Park, CA (US); Joseph C. McAuliffe, Sunnyvale, CA (US); Wyatt Charles Smith, Tiburon, CA (US)

(73) Assignee: Danisco US Inc., Palo Alto, CA (US)

( * ) Notice: Subject to any disclaimer, the term of this patent is extended or adjusted under 35 U.S.C. 154(b) by 0 days.

(21) Appl. No.: 12/113,789

(22) Filed: May 1, 2008

(65) Prior Publication Data

US 2009/0054560 A1    Feb. 26, 2009

Related U.S. Application Data

(62) Division of application No. 10/724,271, filed on Nov. 26, 2003, now Pat. No. 7,378,219.

(60) Provisional application No. 60/429,518, filed on Nov. 26, 2002.

(51) Int. Cl.
    *F21L 4/04*    (2006.01)
(52) U.S. Cl. .................. 430/1; 430/2; 430/270.14; 430/945; 359/3; 362/200; 428/64.8
(58) Field of Classification Search ............... None
    See application file for complete search history.

(56) References Cited

U.S. PATENT DOCUMENTS 5,290,699 A    3/1994    Oesterhelt et al.
5,346,789 A    9/1994    Lewis et al.
5,374,492 A    12/1994   Hampp et al.
5,470,690 A    11/1995   Lewis et al.

(Continued)

FOREIGN PATENT DOCUMENTS

EP    03 79 6535    9/2006

(Continued)

OTHER PUBLICATIONS

Gill et al. "Bio-doped Nanocomposite polymers: Sol-Gel Bioencapsulates", Chem. Mater., vol. 13 pp. 3404-3421 (Jul. 2001).*

(Continued)

*Primary Examiner*—Martin J Angebranndt
(74) *Attorney, Agent, or Firm*—Howrey LLP; Viola T. Kung

(57) ABSTRACT

The present invention relates to materials comprising hydrophilic polymers and immobilized proteorhodopsin and the use of such materials as an optical information carrier. The material comprises one or more hydrophilic polymers that are capable to form a homogeneous phase with proteorhodopsin prior to solidification to a solid form. The hydrophilic polymer, for example, is silica sol-gel, gelatin, polyvinylalcohol, agarose, agar, methyl cellulose, polyvinyl acetate, polyvinyl pyrrolidone, polyethylene glycol, or a mixture thereof. The solid material having immobilized proteorhodopsin is deposited on a substrate selected from the group consisting of glass, paper, metal, fabric material, plastic material, and used as an optical data storage material or a fraud-proof carrier. The present invention further provides a security ink comprising proteorhodopsin and one or more hydrophilic polymers.

9 Claims, 7 Drawing Sheets

U.S. PATENT DOCUMENTS

| | | | | |
|---|---|---|---|---|
| 5,518,858 | A | * | 5/1996 | Dyukova et al. ............. 430/167 |
| 6,140,012 | A | * | 10/2000 | Smithey et al. ........ 430/270.14 |
| 6,274,279 | B1 | | 8/2001 | Hampp et al. |
| 6,616,964 | B1 | | 9/2003 | Hampp et al. |
| 7,378,219 | B2 | * | 5/2008 | Jensen et al. ........... 430/270.14 |
| 7,517,968 | B2 | * | 4/2009 | Braiman et al. ............. 530/418 |
| 2005/0095605 | A1 | | 5/2005 | Jensen et al. |

FOREIGN PATENT DOCUMENTS

| | | |
|---|---|---|
| JP | A-60-184256 | 9/1985 |
| WO | WO 94/05008 | 3/1994 |
| WO | 00/59731 | 10/2000 |
| WO | WO 01/83701 A2 | 11/2001 |
| WO | WO 03/002351 A1 | 1/2003 |

OTHER PUBLICATIONS

Kunugi et al., "Orientation and immobilization of bacteriorhodopsin in polyacrylamide gel membranes", Poly. Bull., vol. 19 pp. 417-421 (1988).*

Birge High Speed random access, fourier transfer holographic associative and high density two-photon three dimensional optical memories based on bacteriorhodopsin, RL-TR-95-6 Final Technical Report (Jan. 1995) 33 pages.*

Bejà, et al., "Bacterial Rhodopsin: Evidence for a New Type of Phototrophy in Sea," in Science, 289, 1902-6 (2000).

Bejà, et al., "Proteorhodopsin Phototrophy in Ocean," in Nature, 411, 786-9 (2001).

Cullin, et al., "Optical properties of Triton X-100 treated purple membranes embedded in gelatin films," Supramolecular Sci., 2(1): 25-32 (1995).

Dioumaev, et al., "Proton Transfers in the Photochemical Reaction Cycle of Proteorhodopsin," Biochem, 41, 5348-58 (2002).

Dioumaev, et al., "Proton Transport by Proteorhodopsin Requires that Renital Schiff Base Cunterion Asp-97 Be Anionic," Am. Chem. Society, 42, 6582-7 (2003).

Downie, et al., "Measurements of holographic properties of bacteriorhodopsin films," Applied Optics, 35(29): 5780-9 (1996).

Friedrich, et al., "Proteorhodopsin is a Light-driven Proton Pump with Variable Vectoriality," J. Mol. Biol., 321, 821-38 (2002).

Gill, et al., "Encapsulation of Biologicals within Silicate, Siloxane, and Hybrid Sol—Gel Polymers: An Efficient and Generic Approach," J. Amer. Chem. Society, 120, 8587-98 (1998).

Hampp, "Bacteriorhodopsin as a Photochromic Retinal Protein for Optical Memories," Amer. Chem. Society, 100, 1755-76 (2000).

Hampp, "Bacteriorhodopsin: mutating a biomaterial into an optoelectronic material," Appl. Microbiol. Biotechnol, 53, 633-9 (2000).

Man, et al., "Diversification and spectral tuning in marine proteorhodopsins," J. EMBO, 22, 1725-31 (2003).

Sabehi, et al., "Novel Proteorhodopsin variants from Mediterranean and Red Seas," Environmental Microbiol., 5(10): 842-9 (2003).

Váró, et al., "Characterization of Photochemical Reaction Cycle of Proteorhodopsin," J. Biophysical, 84, 1202-7 (2003).

Shimono, et al., "Functional expression of pharonis phoborhodoppsin in Eshericha coli, FEBS Lett., vol. 420(1) pp. 54-56 (1997).

Dencher, et al., Formation and properties of bacteriorhodopsin monomers in the non-ionic detergents octyl-b-glucoside and triton X-100, FEBS Lett, vol. 96(2) pp. 322-326 (Dec. 1978).

Oesterhelt, Dieter, Christoph Bräuchle, and Norbert Hampp, "Bacteriorhodopsin: a biological material for information processing," Quarterly Reports of Biophysics 24, 4 (1991) pp. 425-478.

Wu, et al., "Bacteriorhodopsin encapsulated in transparent solgel glass: A new biomaterial", Chem. Mater. vol. 5 pp. 115-120 (1993).

Weetall, "D96N mutant bacteriorhodopsin immobilized in sol-gel glass characterization", Appl. Biochem. Biotechnol., vol. 49(1-3) p. 241-256 (1994).

Kuo, Sheng-Chu et al., "Synthesis and Antiplatelets Activity of Ethyl 4(1-benzyl-1h-indazol-3-yl)benzoate (YD-3) Analogues", Doctor and Master Thesis, China Medical University, Graduate Institute of Pharmaceutical Chemistry, Taiwan, pp. 21, 23 (with English.

Krebs, et al., "Detection of fast light-activated H+ release and M intermediate formation from Proteorphodopsin," BioMed. Central Physiol., 2, 1-8 (2002).

Juchem, et al., "Reflection-type polarization holograms in bacteriorhodopsin films for low-light recording," Optical Society of Amer., 26(21): 1702-04 (2001).

Hampp, "Printing Inks Containing the Photochromic Protein Bacteriorhodopsin," Proc. SPIE, 3979, 118-25 (2000).

Krebs, et al., Resonance Raman Characterization of Proteorhodopsin's Chromophore Environment, J. Phys. Chem. B G, 107, 7877-83 (2003).

Laemmli, U. K., "Cleavage of Structural Proteins during the Assembly of the Head of Bacteriophage T4," in Nature, 227, 680-85 (1970).

* cited by examiner

METHOD FOR PREPARING SOLID MATERIALS COMPRISING IMMOBILIZED PROTEORHODOPSIN

This application is a divisional of U.S. application Ser. No. 10/724,271, filed Nov. 26, 2003 now U.S. Pat. No. 7,378,219; which claims the benefit of U.S. Provisional Application No. 60/429,518, filed Nov. 26, 2002. The contents of the above-identified applications are incorporated herein by reference in their entirety.

FIELD OF INVENTION

The present invention relates to materials comprising hydrophilic polymers and immobilized proteorhodopsin and the use of such materials as an optical information carrier. Particularly, the invention relates to use of immobilized proteorhodopsin as optical data storage materials or fraud-proof optical data carriers.

BACKGROUND OF THE INVENTION

Bacteriorhodopsin (BR) is a retinal protein molecule found in the photosynthetic system of a salt-marsh bacterium called *Halobacterium salinarium*. The BR molecules are located in the cell membrane, forming a 2D protein-lipid array, commonly called the purple membrane. The use of photochromic proteins like bacteriorhodopsin (BR) for optical data storage has been considered promising. BR-based optical films have been worked on for the past two decades, but they do not have the required properties to make them commercially viable for data storage applications. One of the problems with the BR-based films is that BR forms 0.2-1 μm sized protein-lipid patches. If BR is extracted from these patches to form a monomeric protein, it becomes unstable and is inactivated in a few days. The problem with using these BR patches in optical films is that the patches are approximately the same size as the wavelength of the light used to interface the film. This results in significant light scattering during read and write cycles, thereby increasing noise and degrading the performance of the film. Additionally, the BR patches tend to stick to each other, which result in uneven distribution of the BR protein in the film, and further degrade the performance of BR-based optical films.

Another problem of BR is that it is expensive to produce in large quantity. BR has to be expressed in its natural organism *H. salinarum* for it to be fully functional (Dunn, et al., *J Biol Chem*, 262: 9246-9254 (1987); Hohenfeld, et al., *FEBS Lett*, 442: 198-202 (1999)). *H. salinarum* grows very slowly, gives a low cell density and requires the presence of large amounts of salt in the growth medium. The low productivity of *H. salinarum* and the need for expensive custom-made fermentation and recovery equipment that can tolerate the high salt growth medium result in high cost of BR production.

Proteorhodopsins (PRs) are distantly related to bacteriorhodopsin (22-24% sequence identity). Proteorhodopsins are integral membrane proteins; they are isolated from uncultivated marine eubacteria and function as light-driven proton pumps. Upon absorption of light by the all-trans-retinal cofactor, proteorhodopsin goes through a photocycle with a number of intermediates. It is believed that upon excitation of the proteorhodopsin molecule by light stimulation, a proteorhodopsin/retinal complex is excited to an unstable intermediate energy state. Proteorhodopsin progresses through a series of unstable energy states that can vary in terms of energy plateaus or intermediates, e.g., an "M-like state" or "M-state", a "K-like state" or "K-state", an "N-like state" or "N-state", or an "O-like state" or "O-state". Subsequently, the complex reverts to a more stable basal state concomitant with transportation of a proton.

Proteorhodopsin and bacteriorhodopsin are different families of proteins. These proteins have some shared characteristics, but also have clearly different properties. Proteorhodopsins are more advantageous to use in some technical applications than bacteriorhodopsins because of the ease of expressing and producing proteorhodopsins. Proteorhodopsin can be functionally expressed in *E. coli*, a bacterial host capable of rapid high-level protein expression. Thus, production of proteorhodopsin is more economic and efficient than production of bacteriorhodopsin.

Béjà, et al. (*Science* 289:1902-6, 2000) disclose the cloning of a proteorhodopsin gene from an uncultivated member of the marine γ-proteobacteria (i.e., the "SAR86" group). The proteorhodopsin was functionally expressed in *E. coli* and bound all-trans-retinal to form an active light-driven proton pump.

Béjà, et al. (*Nature* 411:786-9, 2001) disclose the cloning of over twenty variant proteorhodopsin genes from various sources. The proteorhodopsin variants appear to belong to an extensive family of globally distributed proteorhodopsin variants that maximally absorb light at different wavelengths.

Dioumaev, et al. (Biochemistry, 42: 6582-6587 (2003)) disclose using proteorhodopsin-containing membrane fragments encased in polyacrylamide gel for flash photolysis and measurements of absorption changes in the visible range.

Optical data storage has the potential to revolutionize the computer industry, since optical data storage provides both a very high storage capacity and rapid reading and writing of data. Additionally, optical signal processing could be used in a highly parallel fashion for pattern recognition, which is difficult to do with the current computing technologies. A functional optical material with low light scattering is required for these applications to succeed.

Documents like banknotes, checks, identity cards etc. often incorporate security features to make them difficult to copy or counterfeit. Most of these are based on either using special paper with security features like watermarks incorporated during paper manufacturing, or printing hairline patterns that are difficult to copy. However, such features are permanently visible and do not meet security requirements.

There are needs for optical information carriers that can be produced efficiently and economically and have low background noise. Such optical information carriers are effective as optical data storage material or fraud-proof optical data carriers.

SUMMARY OF THE INVENTION

The present invention is directed to an optical information carrier comprising a solid material having immobilized proteorhodopsin. The solid material comprises one or more hydrophilic polymers that are capable of forming a homogeneous phase with proteorhodopsin prior to solidification to a solid form. The hydrophilic polymer, for example, is silica sol-gel, gelatin, polyvinylalcohol, agarose, agar, methyl cellulose, polyvinyl acetate, polyvinyl pyrrolidone, polyethylene glycol, or a mixture thereof.

The solid material having immobilized proteorhodopsin is deposited on a substrate such as glass, paper, metal, fabric material, plastics. For example, the immobilized proteorhodopsin can be deposited on a document, a disk, a card or cast in a mold and is used as an optical data storage material or a fraud-proof carrier.

As an optical data storage material, detergent-solubilized proteorhodopsin, which is in a monomer or an oligomer form, is preferred. The monomer or an oligomer form of PR is stable for at least one month at room temperature or one year at 4° C. The optical data storage material comprising detergent-solubilized proteorhodopsin is advantageous in that it does not cause light scattering, thus providing a good signal-to-noise ratio.

The present invention provides a method for preparing a solid material containing a hydrophilic polymer and immobilized proteorhodopsin. The method comprises the steps of: mixing a hydrophilic polymer or its precursor with proteorhodopsin in an aqueous solution to form a homogeneous solution; and solidifying the solution, whereby the proteorhodopsin is immobilized in the hydrophilic polymer. The solidifying includes the processes of polymerizing, cooling, drying, or curing.

The present invention further provides a security ink comprising proteorhodopsin and one or more hydrophilic polymers, wherein the proteorhodopsin and the hydrophilic polymers form a homogeneous liquid phase, said ink solidifies or dries after application onto a surface, thereby immobilizing proteorhodopsin onto a specific location where the ink is applied.

In one embodiment, the invention provides a material suitable for an optical information carrier. Particularly, the material is suitable for optical data storage material or fraud-proof optical data carrier.

In one embodiment, the invention provides material suitable for the processing and storage of optical information.

In one embodiment, the invention provides a stabilized intermediate state (M state) for molecular information storage and processing.

In one embodiment, the invention provides a material for use in storing (writing) optical data, the material being capable of retaining data while permitting nondestructive detection (reading) of such data, and being capable of reuse after optical erasure of data.

In one embodiment, the invention provides a method for nondestructively reading information stored in an optical memory system, both in a two-dimensional and in a three-dimensional manner.

In one embodiment, the invention provides an information carrier material that is difficult for counterfeiters to mimic.

In one embodiment, the invention provides fraud-proof ink that changes color upon exposing to light.

ABBREVIATIONS

CAPS: 3-(cyclohexylamino)-1-propane sulfonic acid
CHES: 2-(N-cyclohexlamino)ethane sulfonic acid
EDTA: Ethylenediaminetetraacetate
IPTG: Isopropyl β-D-thiogalactopyranoside
MES: 2-(N-morpholino)ethane sulfonic acid
TRIS: Tris Hydroxymethylaminoethane
PR: Proteorhodopsin

DETAILED DESCRIPTION OF THE INVENTION

Figure 1:
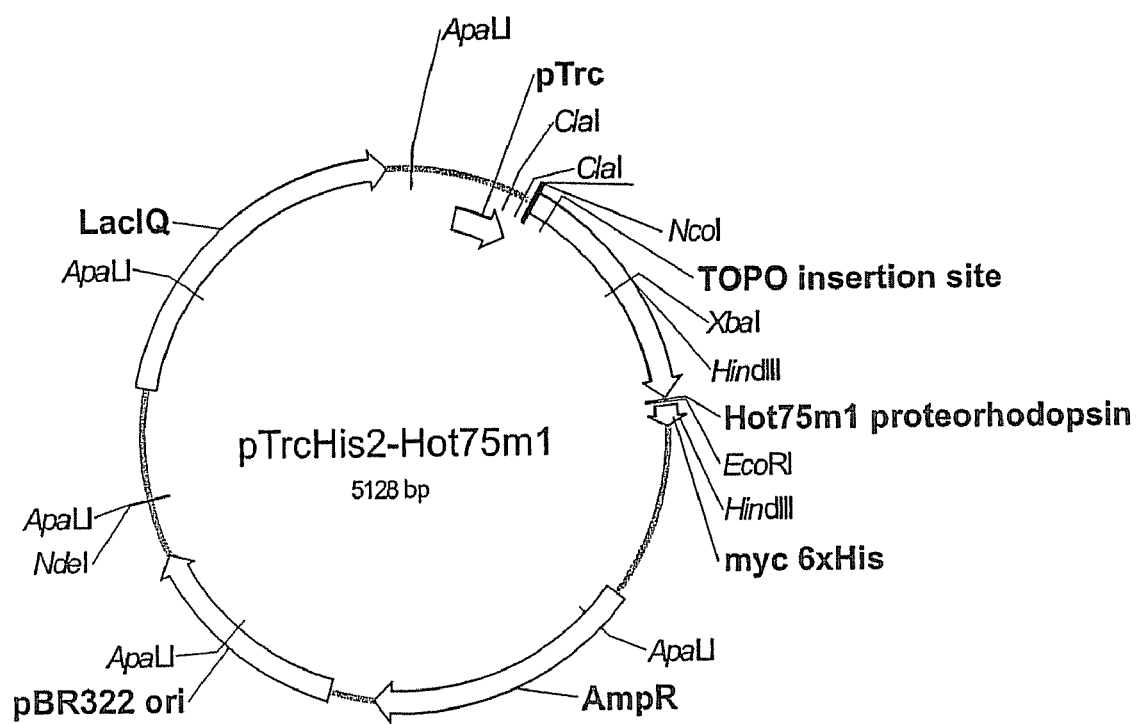
FIG. 1 shows a map of the expression plasmid pTrcHis2-Hot75 ml.

The present invention provides an optical information carrier comprising a solid material having immobilized proteorhodopsin. The solid material comprises one or more hydrophilic polymers that are capable of forming a homogeneous phase with proteorhodopsin prior to solidification to a solid form such that the proteorhodopsin molecules are evenly distributed in the solid. By "homogeneous" is meant that the proteorhodopsin and the hydrophilic polymer or its precursor form a uniform structure or composition throughout the mixture.

The hydrophilic polymers produce a non-opaque or optically transparent solid material, which allows efficient light excitation.

Hydrophilic polymers suitable for this invention include silica sol gel, gelatin, polyacrylamide, acacia, agar, calcium carrageenan, calcium alginate, sodium alginate or other salts of alginic acid, algin, agarose, collagen, methyl cellulose, polyethylene glycol, sodium carboxy methyl cellulose, polyacrylic acid, partially cross-linked polyacrylic acid, hydroxyethyl cellulose, hydroxypropyl cellulose, hydroxypropylmethyl cellulose, polyethylene oxide, pectin and mixtures thereof.

Vinyl polymers and derivatives thereof are also useful in the present invention. Polyvinyl alcohol (PVA), is defined as a homopolymer or copolymer, in which vinyl acetate is a starting monomer unit and in which most or all (70-100%) of the acetate moieties are subsequently hydrolyzed to alcohol moieties. Other vinyl polymers useful in the present invention include, but are not limited to, polyvinyl acetate and polyvinyl pyrrolidone. Copolymers such as PVA-methylmethacrylate copolymer may also be used in the present invention. PVA is commercially available in a wide range of molecular weights, viscosities and varying degrees of hydrolysis from the polyvinyl acetate precursor.

Other polymers useful for this invention include polymers that form hydrogels such as Carbopol®, acidic carboxy polymers; Cyanamey-O polyacrylamides; cross-linked indene-maleic anhydride polymers, Polyox® polyethylene oxide polymers; starch graft copolymers; Aqua-Keepso acrylate polymer polysaccharides composed of condensed glucose units such as diester cross-linked polyglucan, and the like. Representative polymers that form hydrogel are shown in U.S. Pat. Nos. 3,865,108; 4,002,173; 4,207,893; and in Handbook of Common Polymers, by Scott and Roff, published by the Chemical Rubber Company, Cleveland, Ohio.

The present invention provides an optical information carrier comprising a solid material containing immobilized proteorhodopsin. The solid material can range in thickness from a thinly deposited layer orders of magnitude larger in two dimensions than in the third dimension to a thickly cast object with all dimensions of comparable magnitude. Immobilized, as used herein, means that proteorhodopsin is not mobile, and is fixed within the material. The interaction between proteorhodopsin and the material can be covalent or non-covalent. For example, proteorhodopsin can be physically entrapped within the material. Proteorhodopsin can also bind to the material by electrostatic charges, H-bond, hydrophobic, hydrophilic, or van der Waals interaction. By immobilization, the proteorhodopsin molecules are fixed and do not diffuse or diffuse very slowly within the solid material, such that an optical signal is not lost by diffusion of the proteorhodopsin molecules.

One advantage of using proteorhodopsin as an optical information carrier is that proteorhodopsin can be functionally expressed in E. coli to produce a large quantity (grams or kilograms) of protein economically and efficiently. The proteorhodopsin-expressing cells are lysed and the pellets containing the membrane fraction are collected. The proteorhodopsin protein can be further extracted from the membrane by detergent solubilization. Either the membrane or fragments of membrane that contains proteorhodopsin, or the purified proteorhodopsin protein can be immobilized in a hydrophilic polymer and used as an optical information carrier such as an optical data storage material or a fraud-proof data carrier.

As an optical data storage material, it is desirable to immobilize membrane-free, detergent-solubilized proteorhodopsin to avoid light scattering. Detergent-solubilized proteorhodopsin is usually in the form of a monomer, and sometimes in the form of an oligomer (dimer, trimer, tetramer, pentamer, or hexamer). Different from bacteriorhodopsin, proteorhodopsin protein is stable in its monomeric or oligomeric state for at least one month at room temperature, or one year at 4° C. The term "stable" refers to that proteorhodopsin does not change its spectral property significantly (less than 30 nm in maximum absorption wavelength) and is able to produce a photocycle upon excitation by light that includes a transition from the basal state to M-state. As a comparison, heat-denatured PR has no absorption peak in the 480-530 nm range. Heat-denatured PR molecules do not generate a functional photocycle and have maxima absorption wavelengths between 340-440 nm, often 350-430 nm, and more often 360-420 nm.

As used herein, the term "basal state" or "B-state" or "B-like state" refers to the basal state of the photocycle of a proteorhodopsin molecule without light excitation; the basal absorption maxima of proteorhodopsin variants are in general between 480 nm and 530 nm, often between 488 and 526 nm. The term "M-state" or "M-like state" refers to an excited spectral state in a photocycle as compared with the basal state; the absorption maxima of the M-state of proteorhodopsin variants in general are between 350 nm and 450 nm, often about 410 nm. The M-state is distinguished from other identified spectral states, the K-, N- and O-like states, which all have red-shifted absorption spectra (e.g. >530 nm) compared with the basal state.

When proteorhodopsin is exposed to light of excitation wavelength, it is excited to an activated M-state and changes to a yellow color. The color is reverted to its basal color either spontaneously with time or by exposing the material to a second light. For example, the proteorhodopsin-containing material is excited by a yellow light or a green light to change color from red or purple to yellow; the color change is erased spontaneously or by illuminating the material with purple or blue light. Conventional inks based on pigments or organic dyes cannot mimic this color change. The color change feature makes the proteorhodopsin material difficult for counterfeiters to mimic.

Individual proteorhodopsin monomers are about 50 nm in size; such small size does not cause scattering of light in the visible range. The monomeric or oligomeric stability of proteorhodopsin makes it desirable as a component of an optical data storage material without μm-sized particles that scatter light. Additionally, the small size of the individual proteorhodopsin monomers makes it easier to obtain a uniform protein distribution in the optical data storage material. When exposed to light of wavelength 490-550 nm, a configuration change is induced in the retinal residue of proteorhodopsin. This change in configuration is reversible both thermally and photochemically.

The present invention provides a method for preparing a solid material containing immobilized proteorhodopsin in a hydrophilic polymer or in a mixture of hydrophilic polymers. The method comprises the steps of first mixing a hydrophilic polymer or its precursor with proteorhodopsin in water or an aqueous buffer to form a homogeneous solution, then solidifying the polymer, wherein the proteorhodopsin molecules are immobilized in the polymer. The solidification of the polymer is carried out by drying, cooling, curing, or polymerization. The present invention is exemplified by a method for preparing a material containing immobilized proteorhodopsin in polyvinyl alcohol. The method comprises the steps of (a) mixing polyvinyl alcohol, water or a buffer having pH between about 3-12, and proteorhodopsin to form a solution; (b) spreading the solution on the surface of a solid; and (c) drying the solution to form a polyvinyl alcohol material containing immobilized proteorhodopsin.

The present invention is also exemplified by a method for preparing a polyacrylamide material that contains immobilized proteorhodopsin. The method comprises the steps of (a) mixing acrylamide, bisacrylamide, membrane-free proteorhodopsin, and one or more polymerization initiators in water or a buffer having pH between 3-12; and (b) polymerizing acrylamide gel; whereby the proteorhodopsin is immobilized within the polyacrylamide gel matrix. The polymerization initiators commonly used include ammonium persulfate and N,N,N',N'-tetramethylethylenediamine (TEMED). Alternatively, the method comprises the steps of (a) mixing acrylamide, bisacrylamide, membrane-free proteorhodopsin, and one or more UV-activated free radical generators in water or a buffer having pH between 3-12; and (b) exposing the mixture to UV light to polymerize acrylamide gel. The UV-activated free radical generators include riboflavin and TEMED (used together), 2,2-Dimethoxy-2-phenyl acetophenone (DMPA), and those described in the SE96047-3 patent.

The present invention is further exemplified by a method for preparing a sol-gel that contains immobilized proteorhodopsin. The method comprises the steps of: (a) adding to a silane precursor an acidic solution having pH 1.5-4 to hydrolyze the silane precursor to form silicate sol; (b) adding to the silicate sol an aqueous solution containing proteorhodopsin at pH about 5-9; and (c) incubating (b) to form a gel; whereby the proteorhodopsin is immobilized within the sol gel matrix. The silane precursors include tetraallylorthosilicate, alkyltrialkoxysilane, aryltrialkoxysilane, dialkyldialkoxysilane, diaryldialkoxysilane, alkali metal silicate, polyol silicate, polyol siloxane, poly(methyl silicate), and alcohol-free poly(silicic acid). Preferred silane precursors are tetraalkylorthosilicate and poly(glyceryl)silicate.

The present invention is additionally exemplified by a method for preparing gelatin containing immobilized proteorhodopsin. The method comprises the steps of: (a) heating and dissolving gelatin in water or a buffer to form a homogeneous aqueous gelatin solution; (b) cooling the gelatin solution to about 39-45° C.; (c) mixing the cooled gelatin solution with proteorhodopsin; and (d) incubating (c) to form a gel; whereby the proteorhodopsin is immobilized within the gelatin gel matrix.

The material containing immobilized proteorhodopsin can be spread or sprayed on the surface of a document, a disk, and a card for use as an optical data storage material. In one embodiment, the material can be used in a volumetric data storage device or a holographic data storage device. A volumetric data storage device is a type of a 3D data storage device, in which a thickness of the data-recording material is divided into a number of virtual planes that each contains stored data. A volumetric data storage device is therefore comparable to a stack of 2D storage devices. A holographic data storage device is another type of 3D data storage device; it uses the thickness of the film by recording the 3D interference pattern of a data carrying and a reference light beam.

The material containing immobilized proteorhodopsin can be spread, sprayed, solidified, printed, deposited or dried on the surface of glass, paper, fabric materials, plastic material, metal surface or mineral surface for use as a fraud-proof data carrier.

The material containing immobilized proteorhodopsin can also be shaped in a mold to form the three-dimensional optical storage material or the fraud-proof data carrier.

The present invention provides an optical information carrier comprising a solid material having immobilized proteorhodopsin and a substrate such as glass, paper, metal, fabric material, plastic material, wherein said solid material is deposited on said substrate. For example, the substrate is a disk, a card, or a document. In one embodiment of the invention, the solid material comprises one or more hydrophilic polymers or precursors that are capable of forming a homogeneous phase with proteorhodopsin prior to solidification to a solid form.

The optical information carrier of the present invention may be in the form of a thin film or membrane, which may be referred to as a two-dimensional film, or may be in the form of a thick film which may be referred to as a three-dimensional layer or block. The optical information carrier so produced includes proteorhodopsin molecules that can then be exposed to light to convert the molecules from the basal state to the M state.

An alkaline pH such as pH 8-12 of the optical information carrier delays the decay of the light-induced M state, stabilizing the M-state and making it possible to imprint long-lasting optical images on the PR-containing film, even at room temperature. An alkaline pH is effective for optical data storage because of longer lifetime of M-state. The desirable length of time for data storage depends on the application and can vary between a few seconds, a few minutes, a few hours, a few days, a few months, up to a few years. For fraud-proof application, short lifetime of M-state (a few seconds to several minutes) is preferred.

Data are written in the optical information carrier of the present invention optically by exposing specific areas of the proteorhodopsin-containing material briefly to either polychromatic yellow or green light (e.g. from a halogen lamp with a 450 nm cut-on filter) or monochromatic green light (e.g. from a green Diode Pumped Solid State Frequency Doubled (DPSSFD) laser with a wavelength of 532 nm). The exposed area becomes yellow, showing that proteorhodopsin in that area is converted to the activated M intermediate. This is the act of writing data to the proteorhodopsin-containing material. Observing the color of the different areas of the film (e.g. using a video recorder) is a method of reading of the optical data written in the film.

In the absence of light exposure, the proteorhodopsin-containing material gradually reverted to the basal color in about 1-2 minutes. When the proteorhodopsin-containing material in the excited (yellow) state is exposed briefly (less than about a second) to purple light (e.g. from a halogen lamp with a 456 nm cut-off filter) or blue light (e.g. from a blue light emitting diode (LED)), the color of the proteorhodopsin-containing material reverted to the basal color. This corresponds to rapid erasing of the optical signal imprinted in the film. These cycles can be repeated, thereby providing a writable, readable, erasable, and rewritable optical material.

The image formed on the film can represent any kind of information that can be formed as individual data points on the individual PR molecules in the film. The larger the number of individual PR molecules in the film, the greater the optical density (O.D.), and the greater the signal of images stored therein. Selected groups of molecules, and in some cases individual molecules, can represent a pixel of data. By controlling the location and wavelength of the incident light, individual pixels can be selected and exposed for writing information, for reading previously written, or stored, information, or for erasing it. Because each molecule is affected only by light incident on it, and not by the state of the next adjacent molecule, image or data storage resolution is high. The limiting factors for resolution are the density of molecules in the film and the ability of the light source to address a spot as small as a molecule. Another limiting factor for resolution is the background noise due to light scattering. By using the detergent-solubilized, membrane-free form of PR, the light scattering is minimized, thus increasing the signal to noise ratio of the stored data.

The present invention provides an optical data storage device comprising a light source and an optical data information carrier having a solid material containing immobilized proteorhodopsin. The light source emits a writing light to convert the proteorhodopsin from a basal state to a M-state. The device further comprises a second light source that emits a deleting light to convert the M-state into basal state.

The present invention provides a fraud-proof data carrier comprising a solid material having immobilized proteorhodopsin. The solid material is deposited on paper, fabric, plastic, metal surfaces, or mineral surfaces. For example, the solid material is deposited on products such as banknotes, documents, ID cards, passports, drivers' licenses, keycards, checks, securities, stickers, foils, containers, product packing materials etc., to guarantee the authenticity of the products. By using a solid material containing the photochromic protein proteorhodopsin, a color change is obtained when the material is exposed to light having excitation wavelength of the proteorhodopsin. The color change is reversible between the basal state and M-state, which provides protection against falsification. The write-read-erase cycle can be repeated multiple times without any observable change in the property of the material.

As an added security, solid materials containing different proteorhodopsin variants can be deposited at different localized surface regions on banknotes, ID cards, passports, drivers' licenses, keycards, checks, securities, stickers, foils, containers, etc. Unlike bacteriorhodopsin variants, which all have virtually identical spectral properties, proteorhodopsin variants have different spectral properties and different colors (Table 1). Table 1 shows the typical colors corresponding to the absorption wavelengths; however, the actual visual perception may vary. Thus, with different proteorhodopsin variants, it is possible to make multi-color security features on different localized regions of a single fraud-proof document, instead of a single color. The multi-color security features make the forgery even more difficult.

TABLE 1

Spectral Property and color of Proteorhodopsin Variants

| Protein | Absorbance maximum at basic pH (nm) | Color |
|---|---|---|
| Bac31A8 | 521 | Purple |
| Bac40E8 | 519 | Purple |
| Bac64A5 | 519 | Purple |
| Hot0m1 | 518 | Purple |
| Hot75m1 | 493 | Red |
| Hot75m3 | 488 | Red |
| Hot75m4 | 490 | Red |
| Hot75m8 | 493 | Red |
| MB0m1 | 518 | Purple |
| MB0m2 | 523 | Purple |
| MB20m2 | 523 | Purple |
| MB20m5 | 526 | Purple |
| MB20m12 | 524 | Purple |
| MB40m1 | 519 | Purple |
| MB40m5 | 525 | Purple |
| MB40m12 | 523 | Purple |
| MB100m5 | 523 | Purple |
| MB100m7 | 524 | Purple |
| MB100m9 | 524 | Purple |
| MB100m10 | 524 | Purple |
| PalE6 | 490 | Red |

The present invention further provides security ink comprising proteorhodopsin and one or more hydrophilic polymers in a liquid form; the polymers and the proteorhodopsin form a homogeneous phase. The security ink solidifies or dries after it is applied onto a surface; and the proteorhodopsin is immobilized onto a localized region where the ink is applied to provide the security features. The security ink in general is water-based, which is dried or solidified in air and forms a film. The drying or solidification of the ink results from loss of solvent, polymerization, or curing. The security ink is prepared by mixing proteorhodopsin with one or more hydrophilic polymers in an aqueous solution to form a homogeneous solution. Optionally, auxiliary agents such as binders, UV absorbers or dyes are included in the security ink. Binders increase the binding or adhesion of proteorhodopsin to the surface that the ink is applied upon. Binders useful for the present invention include gum arabic, polyvinyl acetate, polyvinyl alcohol, and polyethylene glycol. UV absorbers protect the proteorhodopsin from UV damage and increase the UV-resistance of the security ink. UV absorbers include benzophenone, hydroxynaphthoquinone, phenylbenzoxazole, cinnamic acid esters, sulfonamide and aminobenzoic acid esters. Dyes modify the visual appearance of the ink. Other additives that may be included in the security ink are optical brighteners, driers, anti-skinning agents, thixotropy promoters, waxes, plasticizers, surfactants, defoaming agents and biocides. The hydrophilic polymers can be any water-compatible polymers in which proteorhodopsin can be evenly dispersed to form a homogeneous solution. Preferably, the solution containing proteorhodopsin and the polymers can be dried in air quickly (within a minute or less) and form a film that allows efficient light absorption to excite the basal state of proteorhodopsin. In one embodiment of the invention, the hydrophilic polymer is gum arabic, polyvinylalcohol, polyvinyl acetate, polyethyleneglycol or polyvinyl pyrrolidone In one embodiment of the invention, the security ink can be printed on paper, foil, glass, metal surface, or plastic.

In another embodiment of the invention, the security ink can be applied via screen-printing or ink jet printing onto a document. At ambient conditions and usual room-light illuminations, the area printed from the security ink appears purple or red color depending on the basal state of the specific proteorhodopsin variant used. However, an increase of the light intensity would lead to a rapid change of the color to yellow (M-state). Therefore, unauthorized copies produced by digital scanning or photocopying of documents printed with security ink usually show a yellow area and are easy to be distinguished from the authentic document.

The present invention also provides a method of optically storing information on a material containing immobilized proteorhodopsin. The method comprises the steps of: (a) directing onto a material containing immobilized proteorhodopsin light of a first spectral range representing optical information to be stored, (b) exposing a selected portion of the proteorhodopsin material to switch from its basal state to its M-state; and (c) storing in said material an optical image representing optical information stored; wherein the stored image comprises M-state material having altered absorption spectra at a second spectral range. The optical image stored can be erased by directing light of the second spectral range onto the material to cause the M-state material to switch back to the basal state, thereby erasing the optical image.

The present invention also provides a method of producing a three-dimensional optical image for information storage. The method comprises the steps of: (a) directing onto a three-dimensional optical information storage material that contains immobilized proteorhodopsin a first spectral range representing optical information to be stored; (b) exposing selected locations and selected layers of the proteorhodopsin material to switch the proteorhodopsin from its basal state to its M-state; and (c) producing in said material a three-dimensional optical image representing optical information stored; wherein the stored image comprises M-state material having altered absorption spectra at a second spectral range.

The present invention also provides a method for measurement of the holographic properties of the optical data storage material prepared by the present invention. An optical measurement setup consists of a green laser, e.g. a Diode Pumped Solid State Frequency Doubled (DPSSFD) laser with a wavelength of 532 nm, or an Argon laser with a wavelength of 515 nm. The collimated light from the laser is expanded and passed through a beam splitter. Using mirrors, the resulting two light columns are combined again, thereby forming a sinusoidal interference pattern. The distance between the lines in the diffraction pattern is control by varying the angle between the two beams. The proteorhodopsin-containing material is exposed to the diffraction pattern, thereby writing an optical signal in the film. The signal is read using either the same laser at a lower light intensity or light absorbed by the yellow M-state of the protein.

By varying the angle between the two interfering light beams and therefore the distance between the lines in the resulting diffraction pattern, the maximum resolution of the proteorhodopsin-containing film is measured, which equals the smallest distance between the lines in the diffraction pattern that can be measured. The sensitivity of the material can be measured by exposing the film to different intensities of light and measuring the efficiency of conversion from the B-state to the M-state. The lifetime of the signal in the material can be measured by briefly exposing the film to the diffraction pattern and then measure the reversal to the basal state. Examples of experimental setups are described in Downie and Smithey, *Applied Optics,* 35, 5780-5789, 1996; Cullin et al., *Supramolecular Science,* 2, 25032, 1995; and Juchem and Hampp, *Optics Letters,* 26, 1702-1704, 2001.

The following examples further illustrate the present invention. These examples are intended merely to be illustrative of the present invention and are not to be construed as being limiting.

EXAMPLES

Example 1

Cloning and Mutagenesis of Proteorhodopsin

Different natural proteorhodopsin genes were PCR amplified using Taq DNA Polymerase (Roche Applied Science) as described by the manufacturer. The primers used to amplify all proteorhodopsin variants were PR-u4 and PR-d2 (see Table 2) and the templates were pCR2.1 containing the relevant proteorhodopsin (Béjà, et al., 2000; Béjà, et al., 2001). The PCR products were cloned in the pTrcHis2 vector using the pTrcHis2 TOPO TA Expression Kit (Invitrogen, Carlsbad, Calif.), as described by the manufacturer. Restriction enzyme digestions of the plasmids were used to identify clones containing the insert in the correct orientation. The plasmids were sequenced using the primers pTrcHis Forward and pTrcHis Reverse to ensure that no sequence variations were introduced during the PCR and cloning procedure. The plasmids contain the pTrc promoter transcribing the proteorhodopsin gene with a C-terminal extension containing a myc epitope and six histidine residues. A map of one of the expression plasmids is shown in FIG. 1.

TABLE 2

SEQUENCES OF OLIGONUCLEOTIDE PRIMERS USED

| Primer name | Sequence (5' to 3') |
|---|---|
| PR-u4 | AAATTATTACTGATATTAG GTAGTG (SEQ ID NO: 1) |
| PR-d2 | AGCATTAGAAGATTCTTTA ACAGC (SEQ ID NO: 2) |
| pTrcHis Forward | GAGGTATATATTAATGTAT CG (SEQ ID NO: 3) |
| pTrcHis Reverse | GATTTAATCTGTATCAGG (SEQ ID NO: 4) |
| 31A8-m1A | CAGTTCCTCTATTAATATG TCAATTCTACTTAATTCTT GCTGCTG (SEQ ID NO: 5) |
| 31A8-m1B | CAGCAGCAAGAATTAAGTA GAATTGACATATTAATAGA GGAACTG (SEQ ID NO: 6) |

The pTrcHis Forward and pTrcHis Reverse oligonucleotides were obtained from Invitrogen, the rest of the oligonucleotides were purchased from Operon, the primers used for site-directed mutagenesis were PAGE purified.

The E108Q Bac31A8 proteorhodopsin mutant has an extended lifetime of the M-intermediate of the photocycle (Dioumaev, et al., *Biochem.* 41:5348-58, 2002). An expression vector encoding this protein was constructed by mutagenesis using the QuickChange Site-Directed Mutagenesis Kit (Stratagene) as described by the manufacturer, resulting in the plasmid named pTrcHis2-Bac31A8 E108Q. The template used was pTrcHis2-Bac31A8 and the primers were 31A8-m1A and 31A8-m1B (see Table 2).

Example 2

Expression of Proteorhodopsin

Pre-Culture:

The proteorhodopsin expression plasmid (e.g. pTrcHis2-Bac31A8 E108Q) was transformed into competent cells of the strain BL21-Codonplus-RIL (Stratagene) as described by the manufacturer. The transformed cells were plated on LA+0.5% glucose+100 μg/ml carbenicillin+25 μg/ml chloramphenicol plates and incubated overnight at 37° C. Cells from these plates were grown in 500 ml LB+0.5% glucose+100 μg/ml carbenicillin+25 μg/ml chloramphenicol+10 μM all-trans-retinal medium in 2-L Erlenmeyer flask at 37° C. for 6 hours, until an OD550 of approximately 1.0 AU was reached and used to seed the fermentor.

Fermentation Medium:

The following components were sterilized together in the fermentor vessel: 45 g $KH_2PO_4$, 12 g citric acid, 12 g $MgSO_4.7H_2O$, 30 g yeast extract, 2.0 g ferric ammonium citrate, 5 mL Mazu DF204 as antifoam, 1.2 g CaClHO, and 7.3 mL sulfuric acid. The pH was raised to 6.8 with 20-28% $NH_4OH$ and the following components were added: 0.3 g carbenicillin, 60 mg chloramphenicol, 42 mg all-trans-Retinal, 60 mL of a solution of trace elements and glucose (from a 60 weight % feed). After inoculation, the volume was 6.0 L and the glucose concentration was 10 g/L. The solution of trace elements contained (g/L): citric acid $H_2O$ (4.0), $MnSO_4H_2O$ (3.0), NaCl (1.0), $FeSO_4$ $7H_2O$ (0.10), $CoCl_2.6H_2O$ (0.10), $ZnSO_4$ $7H_2O$ (0.10), $CuSO_4$ $5H_2O$ (0.010), $H_3BO_3$ (0.010), and $Na_2MoO_4$ $2H_2O$ (0.010).

Fermentation and Growth:

A 15 L stirred tank fermentor was prepared with the medium described above. The temperature was controlled at 37° C. and aqueous ammonia (20-28 weight %) was used to control pH at 6.8. Initial values for air flow rate (set to minimum values of between 6 and 12 standard liters per min) and agitator speed (set to minimum values of between 200 and 690 rpm) were set so that dissolved oxygen (DO) control was initiated when our values reached approximately 140 mmol/L/h. DO control was set at 25%. Glucose was maintained at between 0 g/L and 10 g/L with a 60 weight % feed. Additional 42 mg all-trans-Retinal was added after 8 hours growth. At an OD550 of approximately 60 AU, 0.167 g isopropyl β-D-1-thiogalactopyranoside (IPTG) and 100 mg all-trans-Retinal was added to induce proteorhodopsin expression. App. 3 hours later, additionally 100 mg all-trans-Retinal was added. The fermentation was stopped 3 hours later and the cells were harvested from the broth by centrifugation and stored at −80° C.

Example 3

Purification of Proteorhodopsin

Proteorhodopsin-expressing cells from the fermentor were washed by resuspending 41 g of cells in 160 ml Cell Wash Buffer (50 mM Tris-HCl pH 7.7, Complete, EDTA-free Protease Inhibitor Cocktail Tablets from Roche Applied Science) and pelleted by centrifugation at 8000 g for 10 min.

The cell pellets were resuspended in 160 ml Lysis Buffer (50 mM Tris-HCl pH 7.7, Complete, EDTA-free Protease Inhibitor Cocktail Tablets from Roche Applied Science) and the cell suspension was frozen and thawed three times. The cells were then lysed by passing them through a French press twice in 50 ml batches.

The cells were centrifuged at 15000 g for 1 hour to remove unbroken cells. The supernatant were transferred to ultracentrifuge tubes. There were then centrifuged at 250,000 g for 1 hour to collect membrane pellet.

The pellets containing the membrane fraction were resuspended in 30 ml suspension buffer (50 mM Tris pH 7.7, 2% Dodecyl-beta-D-maltoside, Complete, EDTA-free Protease Inhibitor Cocktail Tablets from Roche Applied Science).

10 ml of Talon Resin (Clontech) was transferred to a column and equilibrated with Resin Wash Buffer (50 mM Tris pH 7.7, 0.1% Dodecyl-beta-D-maltoside, Complete, EDTA-free Protease Inhibitor Cocktail Tablets from Roche Applied Science). The membrane suspension was added to the resin column and incubated for app. 16 hours at 4° C. with gentle inversion mixing.

The resin (in column format) was washed 6 times with 40 ml Resin Wash Buffer suspending the resin after each addition wash. Proteorhodopsin was extracted by adding 10 ml of Extraction Buffer (50 mM Tris pH 7.7, 250 mM EDTA pH 8.0, 0.05% Dodecyl-beta-D-maltoside, 5 mM DTT). The extraction was repeated three times.

The elutates were pooled and EDTA was removed by three successive ten-fold concentrations using Millipore centrifugal filter units and dilutions with Exchange Buffer (20 mM Tris pH 7.7, 1 mM DTT) as described by the manufacturer. The proteorhodopsin samples were then concentrated tenfold and stored at 4° C.

Example 4

Stability of Purified Detergent-Solubilized Proteorhodopsin

Figure 2:
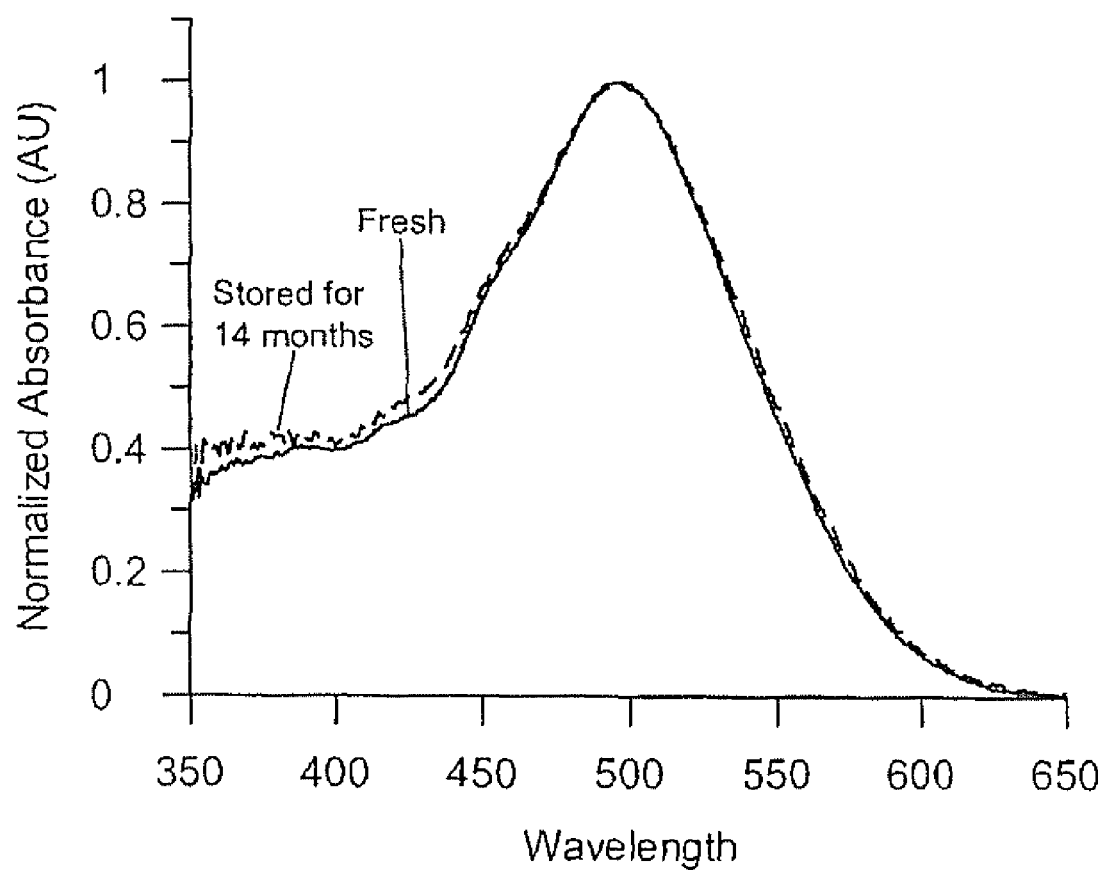
FIG. 2 shows the spectra of Bac31A8 proteorhodopsin preparation before (solid line) and after 14 months storage at 4° C. (dashed line).

Bac31A8 proteorhodopsin was purified using the method described in example 3. The absorbance spectrum of the proteorhodopsin sample was measured both shortly after it was purified and after it had been stored for 14 months at 4° C. The spectra were measured by diluting 5 µl purified proteorhodopsin in 500 µl 100 mM CAPS pH 10, 0.1% Dodecyl-beta-D-maltoside. Wavelength spectra from 350 nm to 650 nm were obtained on a Cary3 spectrophotometer (Varian). FIG. 2 shows the spectra of the same proteorhodopsin preparation before (black line) and after 14 months storage at 4° C. (dashed line). The spectral properties are almost identical between the two samples. Since denaturation of proteorhodopsin results in a change in the spectral properties with a shift in wavelength maximum to approximately 390 nm, it was easily determined that the detergent-solubilized protein is stable under these conditions.

Example 5

Immobilization of Proteorhodopsin Using Polyacrylamide

To immobilized proteorhodopsin using polyacrylamide, the following mixture was prepared:

1.1 ml Duracryl (80% acrylamide 4% bisacrylamide)

0.7 ml Tris/Acetate/MES three-component buffer (1/0.5/0.5 M, pH 9.7)

1.1 ml water 0.5 ml Bac31A8 proteorhodopsin (17.4 mg/ml)

8.8 µl ammonium persulfate (10%)

Polymerization of the gel matrix was initiated with the addition of 2 µl of N,N,N',N'-Tetramethylethylenediamine and mixing immediately. The gel was cast between two glass plates. After polymerization, the gel was removed and dried to atmospheric humidity between sheets of acetate film for use and long-term storage.

Figure 3:
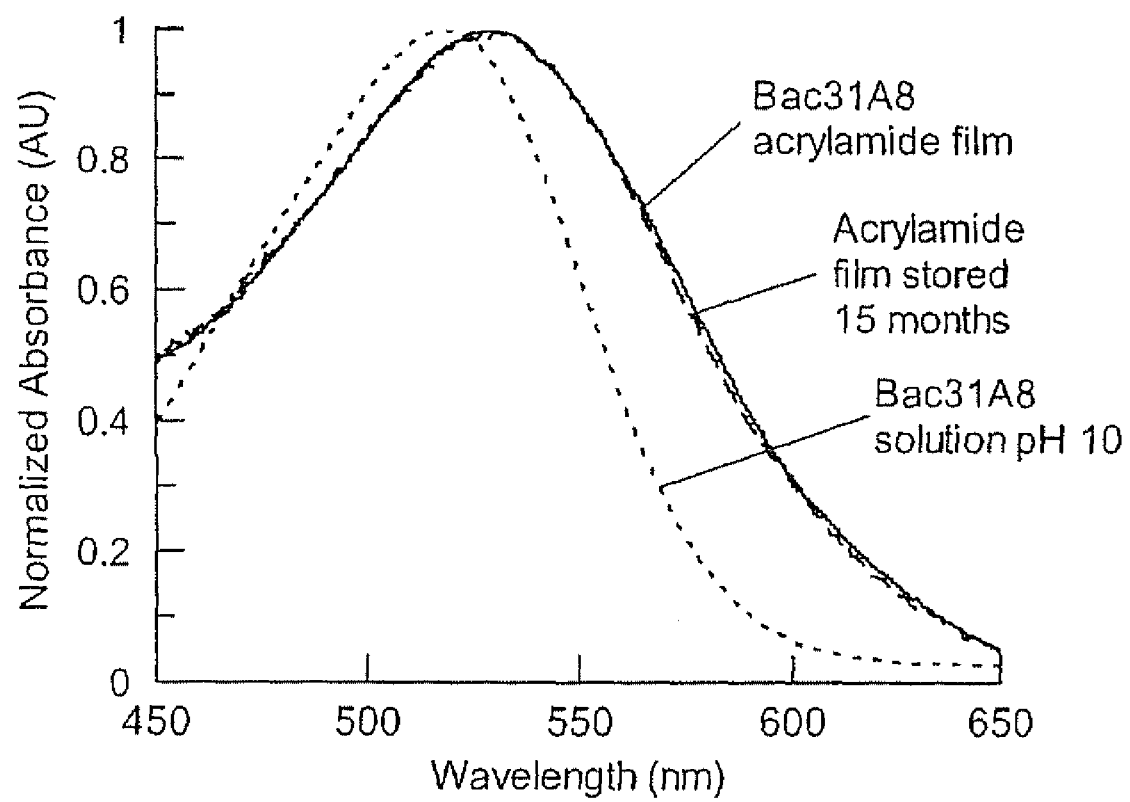
FIG. 3 shows the spectra of (a) Bac31A8 proteorhodopsin in solution at pH 10 (dotted line), (b) freshly prepared Bac31A8 proteorhodopsin immobilized in polyacrylamide (solid line), and (c) Bac31A8 proteorhodopsin immobilized in polyacrylamide stored dry at ambient temperature for 15 months (dashed line).

The dried gel was mounted within a Cary3 spectrophotometer and wavelength spectra were collected. This spectrum was compared to the spectra of a similar sample of proteorhodopsin at the pH of the gel casting (FIG. 3). The difference in these two spectra was, in part, from light scattering but was also likely due to a shift in the pH during drying of the gel and the sensitivity of proteorhodopsin optical spectra to pH. The spectra of proteorhodopsin stored dry at ambient temperature (20-25° C.) for 15 months (dashed line in FIG. 3) was indistinguishable from the freshly prepared sample (solid line in FIG. 3). This showed that proteorhodopsin immobilized in a dried polyacrylamide gel retained its functionality for more than a year when stored at ambient temperature (20-25° C.).

Example 6

Immobilization of Proteorhodopsin Using Silica Sol-Gel

A: A Silicate Sol Containing Proteorhodopsin was Generated from Tetraethylorthosilicate as Follows.

Tetraethylorthosilicate (4.5 mL, 4.2 g, 20.2 mmol) was mixed with deionized water (1.4 mL) and 100 mM hydrochloric acid (100 µL) in a polypropylene vessel and placed in an ultrasound bath for 1 hr. At this point the solution was homogenous and was stored at −20° C. prior to use. Silicate sols prepared in this way were usable for over 6 months when stored at −20° C.

An aliquot of the silicate sol prepared above (240 µL) was added to a solution consisting of 1M potassium phosphate buffer (19.5 µL, pH 7), deionized water (331.5 µL) and a Hot75M1 proteorhodopsin solution (39 µL of 10 mg/mL). The mixture was then placed into a polystyrene cuvette, which was sealed and placed on its side such that the subsequent gelation of the mixture (about 5 minutes) produced a film suitable for continuous optical measurement. The gel was then washed three times with phosphate buffer (100 mM, pH 7) and allowed to cure at 4° C.

Figure 4:
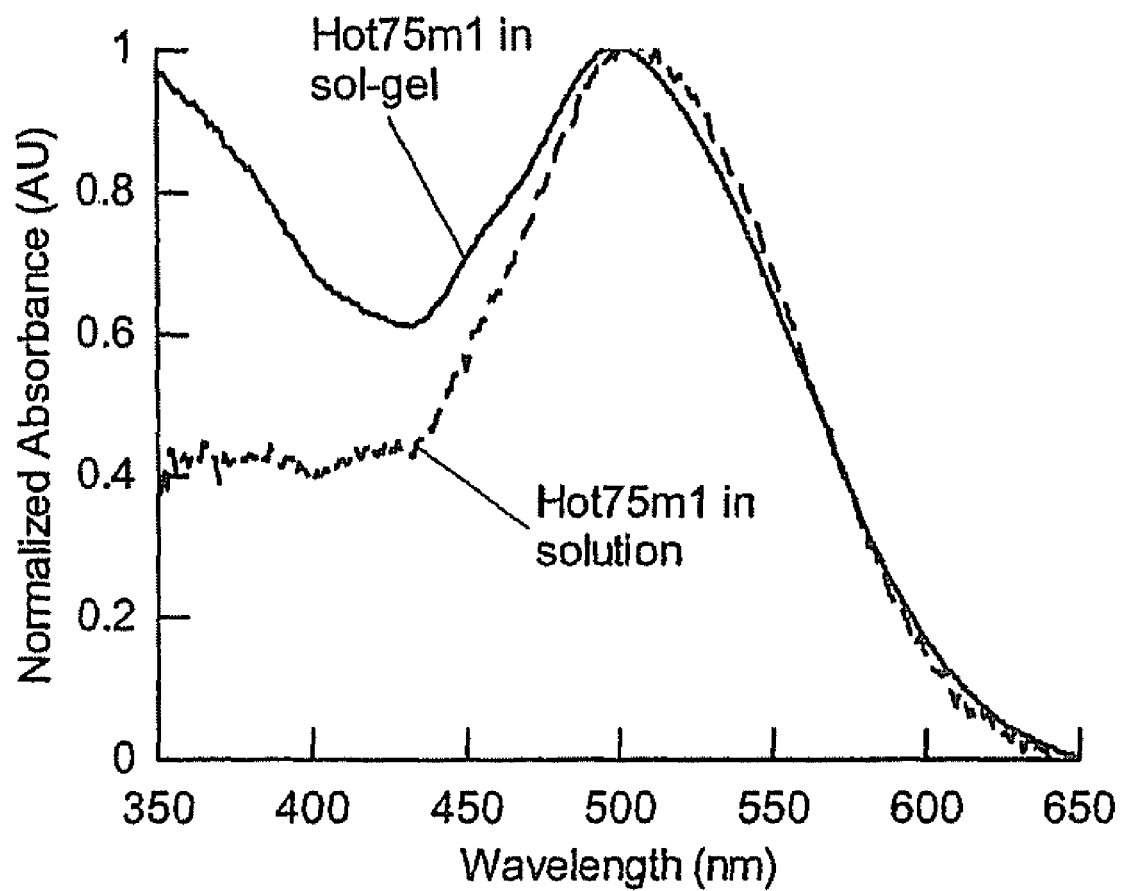
FIG. 4 compares the spectra of Hot75 ml proteorhodopsin in solution and in tetraethylorthosilicate sol-gel.

The sol was equilibrated overnight with pH 9.2 buffer, then placed in a Cary 3 spectrophotometer and spectra collected. This spectrum was compared with purified protein at the same pH (FIG. 4).

The large absorbance values at 450 nm and below are a result of light scattering from particles formed within the gel during gelation. The proteorhodopsin sol-gels produced in this manner retained optical clarity and color for more than 12 months stored at 4° C. providing they were not allowed to dry. No noticeable change in sample color was seen over this period indicating continued stability of the protein in this material.

B: A Poly(glyceryl)silicate (PGS) Sol-Gel Containing Proteorhodopsin was Generated as Follows.

Preparation of the poly(glyceryl)silicate (PGS) precursor was performed according to published procedures (Gill. I. and Ballesteros, A. "Encapsulation of Biologicals within Silicate, Siloxane, and Hybrid Sol-Gel Polymers: An Efficient and Generic Approach" *J. Amer. Chem. Soc.* 1998, 120, 8587-8598). The PGS precursor could be stored for up to 6 months at −20° C. without loss of performance.

All procedures were performed in polypropylene vessels at 4° C. A PGS sol was prepared by mixing the PGS precursor (160 mg) with deionized water (80 μL) until homogenous. Bac31A8 proteorhodopsin (18.2 mg/mL) (39 μL) was mixed with phosphate buffer (1M, pH 7.0) (39 μL) and deionized water (312 μL). This mixture was added quickly to the PGS sol (240 μL), inverted rapidly to mix, and allowed to gel (about 1 to 5 min.). To prepare an aged hydrogel, the container was filled with phosphate buffer (75 mM pH 7.0) and stored at 4° C. (shrinkage was about 20% relative to initial gel volume). To prepare the xerogel, the fresh hydrogel was cured at 4° C. for 1 week then dried in the open air at room temperature (shrinkage was 50-70% relative to initial gel volume). A xerogel is a dried out open structure which has passed a gel stage during preparation.

Figure 5:
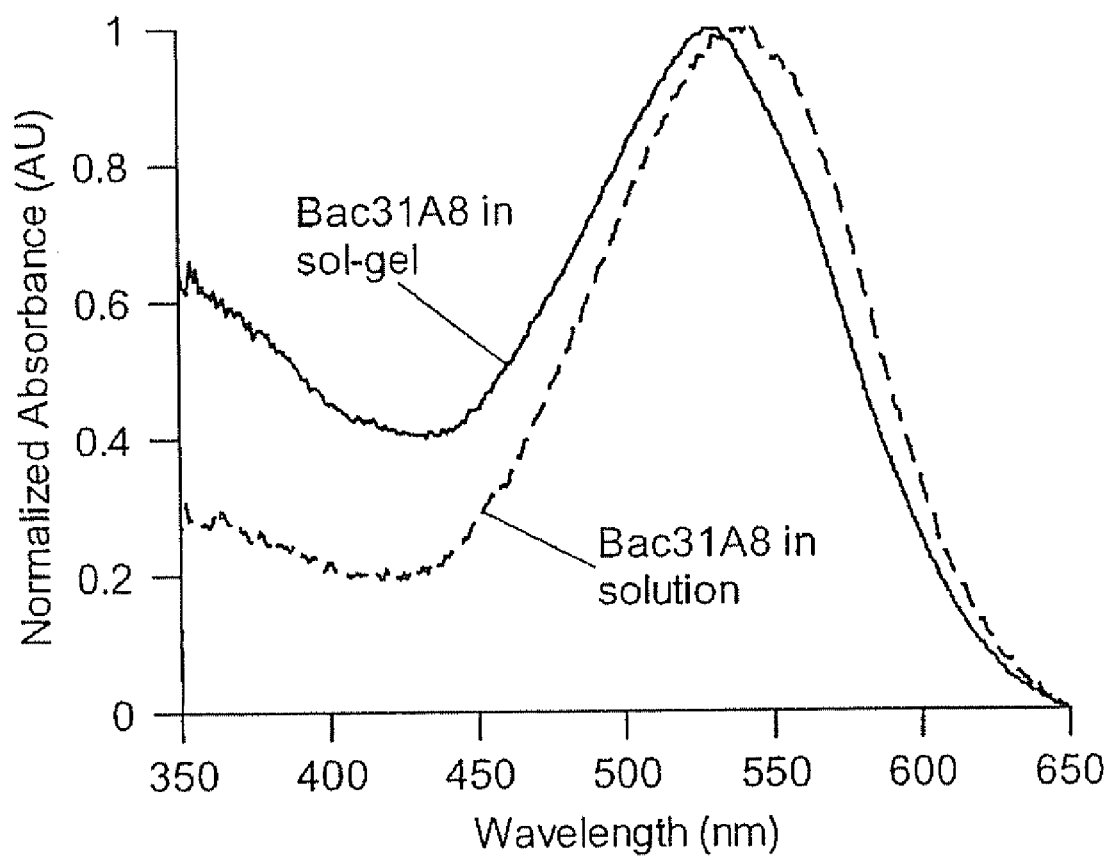
FIG. 5 compares the spectra of Bac31A8 proteorhodopsin in solution and in poly(glyceryl)silicate sol-gel.

The optical spectra of a closed cylindrical glass cuvette (37-PX-5 from Stama Cells, Inc., Atascadero, Calif.) containing a proteorhodopsin encapsulating sol gel stored wet at 4° C. for 12 months was collected using a Cary3 spectrophotometer. The spectrum of the sol gel was compared to that of freshly purified soluble proteorhodopsin (FIG. 5).

The high level of similarity of the spectra of proteorhodopsin in solution and encapsulated in the PGS sol gel indicate that proteorhodopsin was functional in the PGS sol gel. The difference in these two spectra was in part from light scattering but is also likely due to a shift in the pH during curing of the sol gel and the sensitivity of proteorhodopsin optical spectra to pH. The proteorhodopsin sol-gels produced in this manner retained optical clarity and color for more than 12 months stored at either 4° C. or room temperature. No noticeable change in sample color was seen over this period indicating continued stability of the protein in this material.

Example 7

Immobilization of Proteorhodopsin Using Gelatin

E108Q Bac31A8 proteorhodopsin was immobilized in a gelatin film. A 10% solution of gelatin was prepared by dissolving 1.0 g of gelatin (Knox Company; Parsippany, N.J.) in 10 ml of distilled water with heat (approximately 90° C.) and magnetic stirring. The gelatin was allowed to cool to approximately 40° C. with constant stirring.

The following were mixed by magnetic stirring to form a proteorhodopsin containing gelatin matrix:

0.5 ml E108Q Bac31A8 proteorhodopsin (19 mg/ml)

0.4 ml 1 M CAPS buffer pH 10.0

1.1 ml distilled water 2.0 ml 10% gelatin solution (at 40° C.)

This mix was dispensed between two glass plates separated by a watertight, 0.1 cm thick gasket to produce a gelatin film of approximately 10 cm by 4 cm by 0.1 cm thick. The gel was allowed to solidify for 2 hours at 4° C. before the glass plates were separated and one glass plate removed to expose a single surface of the gelatin film.

Figure 6:
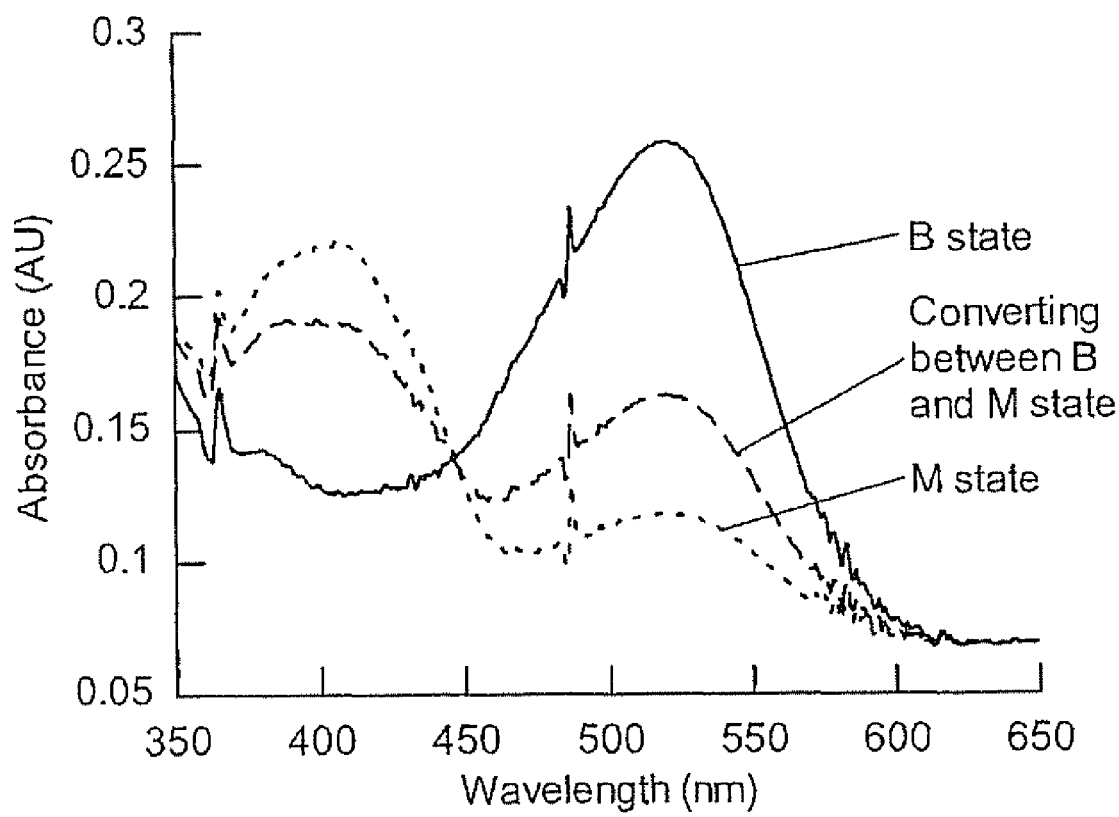
FIG. 6 compares the spectra of the E108Q Bac31A8 proteorhodopsin (immobilized in gelatin) in the B state, in the M state, and in the process of converting from the M state to the B state.

The gelatin film was mounted in the path of a Hewlett Packard 8453 diode array spectrophotometer. The wavelength spectra of E108Q Bac31A8 proteorhodopsin contained in the film was determined. This spectrum of the protein in the B state was compared to spectrum of the protein in the M state (while it was exposed to a bright light source) and a spectrum of the protein sample in the process of converting from the M state to the B state (FIG. 6). Illumination was provided by fiber-optic cables attached to a 150-watt illuminator (Fiber-Lite A3200) from Dolan-Jenner Industries (Lawrence, Mass.) with a 450 nm cut-on colored-glass filter (51284) from Oriel Instruments (Stratford, Conn.). The manual opening and closing of a shutter controlled light exposure.

Figure 7:
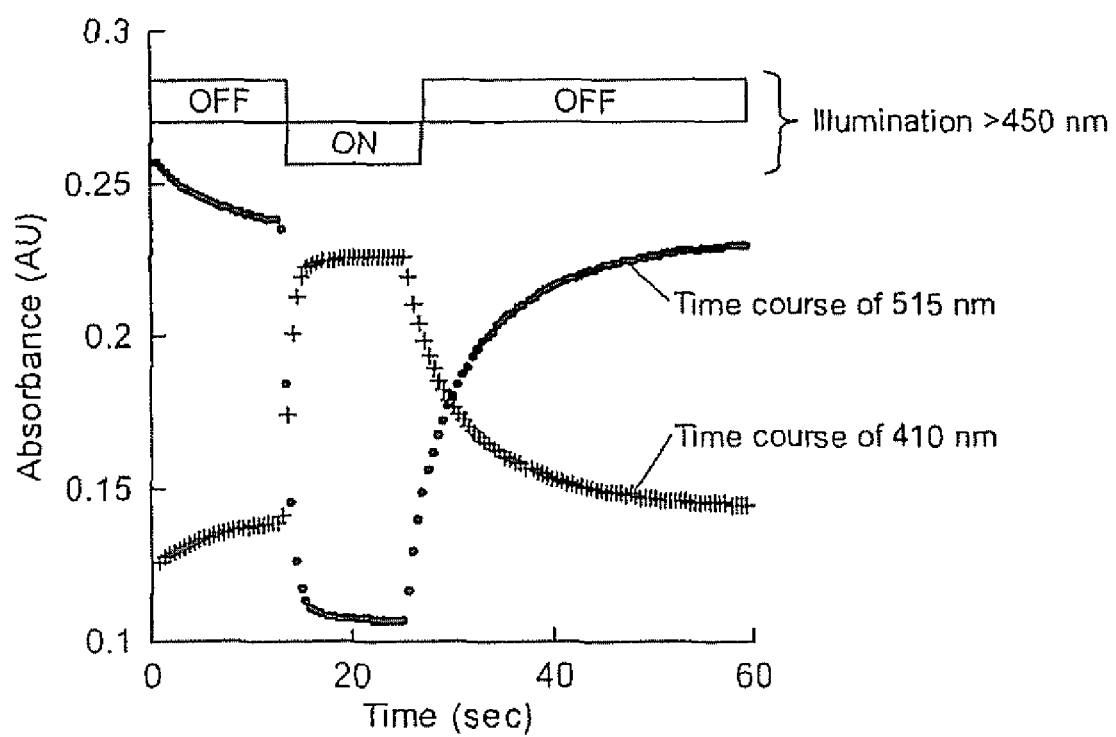
FIG. 7 plots the change of the E108Q Bac31A8 proteorhodopsin (immobilized in gelatin) absorbance at the wavelength maximum of the M state (410 nm) and the B state (515 nm) against time before, during, and after illumination

The change in absorbance at the wavelength maximum of the M state (410 nm) and the B state (515 nm) were plotted against time before, during, and after illumination (FIG. 7).

Using the data after ending continuous illumination, the half-life ($t_{1/2}$) of the M state (time at which half of the sample has converted from the M state back to the B state) was calculated to be 4.15 seconds for these conditions of pH and hydration.

Example 8

Immobilization of Proteorhodopsin Using Polyvinylalcohol

To immobilize proteorhodopsin using polyvinylalcohol (PVA), the following mixture was prepared:

300 μl 15% polyvinylalcohol (average molecular weight 30,000-70,000)

75 μl 1 M CHES buffer pH 10.3

375 μl purified E108Q Bac31A8 proteorhodopsin (19 mg/ml).

The solution was spread on paper, a plastic sheet or a glass plate using a razor blade to form a thin layer of the solution on the material. As an alternative, an airbrush was used to spread the proteorhodopsin-containing material. The material was allowed to dry overnight, forming a film containing proteorhodopsin encapsulated by the PVA polymer.

Example 9

Optical Data Storage Using Proteorhodopsin-PVA Film

The proteorhodopsin-PVA film described in Example 8 was used to show that optical data could be written to and read from a material containing immobilized proteorhodopsin. The proteorhodopsin—PVA film was purple in its initial state. This reflects the majority of the proteorhodopsin molecules being in the basal state (B-state). Data were written in the film optically by exposing specific areas of the proteorhodopsin film briefly to either polychromatic yellow light (from a halogen lamp with a 450 nm cut-on filter) or monochromatic green light (from a green Diode Pumped Solid State Frequency Doubled (DPSSFD) laser with a wavelength of 532 μm). The exposed area became yellow, showing that we successfully had converted proteorhodopsin in that area to the activated M intermediate. This was the act of writing data to the film. Observing the color of the different areas of the film (e.g. using a video recorder) was a method of reading of the optical data written in the film.

In the absence of exposure to blue or purple light, the film spontaneously reverted to the initial purple color in 1-2 minutes. When the proteorhodopsin film in the excited (yellow)

state was exposed briefly (less than a second) to purple light (from a halogen lamp with a 456 nm cut-off filter) or blue light (from a blue light emitting diode (LED)), the color of the film reverted to the initial purple color. This corresponds to rapid erasing of the optical signal imprinted in the film.

Although the invention has been described with reference to the presently preferred embodiments, it should be understood that various modifications can be made without departing from the scope of the invention.

What is claimed is:

1. A method for preparing a solid material containing a hydrophilic polymer and immobilized proteorhodopsin, comprising the steps of:
    mixing a hydrophilic polymer or its precursor with cellular membrane-free proteorhodopsin in a monomer or an oligomer form in an aqueous solution to form a homogeneous solution; and
    solidifying the solution, whereby the proteorhodopsin is immobilized in the hydrophilic polymer.

2. A method for preparing a polyvinyl alcohol material containing immobilized proteorhodopsin, comprising the steps of:
    mixing polyvinyl alcohol, a buffer having pH between 3-12, and cellular membrane-free proteorhodopsin in a monomer or an oligomer form to form a solution;
    dispersing the solution on a solid form; and
    drying the solution to form a material containing immobilized proteorhodopsin.

3. A method for preparing a polyacrylamide material containing immobilized proteorhodopsin, comprising the steps of:
    mixing acrylamide, bisacrylamide, cellular membrane-free proteorhodopsin in a monomer or an oligomer form, and one or more polymerization initiators or a UV-induced polymerization agent in a buffer having pH between 3-12; and
    polymerizing the acrylamide gel;
    whereby the proteorhodopsin is immobilized within the polyacrylamide gel matrix.

4. A method for preparing a sol-gel containing immobilized proteorhodopsin, comprising the steps of:
    (a) adding to a silane precursor an acidic solution having pH 1.5-4 to hydrolyze the silane precursor to form silicate sol;
    (b) adding to the silicate sol an aqueous solution containing cellular membrane-free proteorhodopsin in a monomer or an oligomer form at pH about 5-9; and
    (c) incubating (b) to form gel;
    whereby the proteorhodopsin is immobilized within the sol gel matrix.

5. The method according to claim 4, wherein said silane precursor is tetraalkylorthosilicate, alkyltrialkoxysilane, aryltrialkoxysilane, dialkyldialkoxysilane, diaryldialkoxysilane, alkali metal silicate, polyol silicate, polyol siloxane, poly(methyl silicate), or alcohol-free poly(silicic acid).

6. The method according to claim 5, wherein said silane precursor is tetramethylorthosilicate or tetractholorthosilicate tetraethylorthosilicate.

7. The method according to claim 5, wherein said silane precursor is poly(glyceryl)silicate.

8. A method for preparing gelatin containing immobilized proteorhodopsin, comprising the steps of:
    (a) heating and dissolving gelatin in water or a buffer to form a homogeneous aqueous gelatin solution;
    (b) cooling the gelatin solution to about 39-45° C. and
    (c) mixing the cooled gelatin solution with cellular membrane-free proteorhodopsin in a monomer or an oligomer form; and
    (d) incubating (c) to form gel;
    whereby the proteorhodopsin is immobilized within the gelatin gel matrix.

9. A method for preparing three-dimensional optical data storage material, comprising casting a block of material containing immobilized proteorhodopsin to form a thickly cast optical data storage material, wherein said proteorhodopsin is cellular membrane free, and in a monomer or an oligomer form.

* * * * *

UNITED STATES PATENT AND TRADEMARK OFFICE
CERTIFICATE OF CORRECTION

PATENT NO. : 7,745,066 B2  
APPLICATION NO. : 12/113789  
DATED : June 29, 2010  
INVENTOR(S) : Rasmus B. Jensen et al.

Page 1 of 1

It is certified that error appears in the above-identified patent and that said Letters Patent is hereby corrected as shown below:

On the Title page, correct the Assignee from "Danisco US Inc,." to --Danisco US Inc.--.

Column 20, lines 21 and 22, delete "tetraetholorthosilicate".

Signed and Sealed this  
Nineteenth Day of April, 2011

David J. Kappos  
*Director of the United States Patent and Trademark Office*

SEQUENCE LISTING

```
<160> NUMBER OF SEQ ID NOS: 6

<210> SEQ ID NO 1
<211> LENGTH: 25
<212> TYPE: DNA
<213> ORGANISM: artificial
<220> FEATURE:
<223> OTHER INFORMATION: Primer

<400> SEQUENCE: 1
aaattattac tgatattagg tagtg                                            25

<210> SEQ ID NO 2
<211> LENGTH: 24
<212> TYPE: DNA
<213> ORGANISM: artificial
<220> FEATURE:
<223> OTHER INFORMATION: Primer

<400> SEQUENCE: 2
agcattagaa gattctttaa cagc                                             24

<210> SEQ ID NO 3
<211> LENGTH: 21
<212> TYPE: DNA
<213> ORGANISM: artificial
<220> FEATURE:
<223> OTHER INFORMATION: Primer

<400> SEQUENCE: 3
gaggtatata ttaatgtatc g                                                21

<210> SEQ ID NO 4
<211> LENGTH: 18
<212> TYPE: DNA
<213> ORGANISM: artificial
<220> FEATURE:
<223> OTHER INFORMATION: Primer

<400> SEQUENCE: 4
gatttaatct gtatcagg                                                    18

<210> SEQ ID NO 5
<211> LENGTH: 45
<212> TYPE: DNA
<213> ORGANISM: artificial
<220> FEATURE:
<223> OTHER INFORMATION: Primer

<400> SEQUENCE: 5
cagttcctct attaatatgt caattctact taattcttgc tgctg                      45

<210> SEQ ID NO 6
<211> LENGTH: 45
<212> TYPE: DNA
<213> ORGANISM: artificial
<220> FEATURE:
<223> OTHER INFORMATION: Primer
```

-continued

```
<400> SEQUENCE: 6
cagcagcaag aattaagtag aattgacata ttaatagagg aactg                45
```